(12) United States Patent
Hillairet et al.

(10) Patent No.: US 7,973,115 B2
(45) Date of Patent: Jul. 5, 2011

(54) CATALYST SYSTEMS BASED ON MACROCYCLIC LIGANDS

(75) Inventors: Caroline Hillairet, Soignies (BE); Guillaume Michaud, Lille (FR); Sirol Sabine, Horrues (FR)

(73) Assignee: Total Petrochemicals Research Feluy, Senefe (Feluy) (BG)

( * ) Notice: Subject to any disclaimer, the term of this patent is extended or adjusted under 35 U.S.C. 154(b) by 422 days.

(21) Appl. No.: 11/994,983

(22) PCT Filed: Jul. 3, 2006

(86) PCT No.: PCT/EP2006/063779
§ 371 (c)(1), (2), (4) Date: Aug. 1, 2008

(87) PCT Pub. No.: WO2007/006675
PCT Pub. Date: Jan. 18, 2007

(65) Prior Publication Data
US 2009/0111958 A1   Apr. 30, 2009

(30) Foreign Application Priority Data
Jul. 7, 2005  (EP) .................................... 05106167

(51) Int. Cl.
C08F 4/70 (2006.01)
C08F 4/69 (2006.01)
C08F 4/76 (2006.01)
C08F 4/22 (2006.01)
C08F 4/26 (2006.01)

(52) U.S. Cl. ..................... 526/172; 526/161; 526/169.1; 526/169; 526/169.2

(58) Field of Classification Search .................... 556/51, 556/57, 42, 136, 138; 526/172, 161, 169.1, 526/169, 169.2
See application file for complete search history.

(56) References Cited

U.S. PATENT DOCUMENTS

| | | | |
|---|---|---|---|
| 6,323,309 B1* | 11/2001 | Swager et al. | 528/380 |
| 6,500,909 B2* | 12/2002 | Hirahata et al. | 526/161 |
| 6,593,438 B2* | 7/2003 | Oskam | 526/172 |
| 7,026,415 B2* | 4/2006 | Nagy et al. | 526/172 |
| 7,297,805 B2* | 11/2007 | Kacker et al. | 556/35 |
| 2009/0030172 A1* | 1/2009 | Zheng et al. | 528/271 |
| 2009/0111958 A1* | 4/2009 | Hillairet et al. | 526/172 |
| 2009/0264609 A1* | 10/2009 | Hillairet et al. | 526/172 |

FOREIGN PATENT DOCUMENTS

| | | | |
|---|---|---|---|
| GB | 2 367 818 A | * | 4/2002 |
| JP | 2004-262790 A | * | 9/2004 |
| WO | WO 2007/006740 A1 | * | 1/2007 |

OTHER PUBLICATIONS

Ruther et al. Organometallics 2001, 20, 1247-1250.*
Fuller et al., Angew. Chem., Int. Ed., 2004, 43, 3914-3918.*
Leigh et al., Angew. Chem., Int. Ed., 2001, 40, 1538-1543.*
Zhang et al., Inorg. Chim. Acta, 2003, 351, 201.*
Berg et al., Bioinorganic & Medicinal Chem. Letts., 1998, 8, 1221-1224; abstract only.*
Fuller, "A 3D interlocked structure from a 2D template: Structural requirements for the assembly of a square-planar metal-coordinated [2]rotaxane", Angewandte Chemie, International Edition, 2004, 43, 3914-3918.
Leigh, "Benzylic imine catenates: readily accessible octahedral analogues of the sauvage catenates" Angewandte Chemie, International Edition, 2001, 40, 1538-1543.

* cited by examiner

Primary Examiner — Rip A. Lee

(57) ABSTRACT

The present invention discloses the use of rotoxane ligands to prepare catalyst systems suitable for the oligomerization or polymerization of ethylene and alpha-olefins.

6 Claims, No Drawings

CATALYST SYSTEMS BASED ON MACROCYCLIC LIGANDS

The present invention related to the field of single site catalyst systems based on macrocyclic diimine ligands and suitable for oligomerising or polymerising ethylene and alpha-olefins.

There exists a multitude of catalyst systems available for polymerising or oligomerising ethylene and alpha-olefins, but there is a growing need for finding new systems capable to tailor polymers with very specific properties. More and more post-metallocene catalyst components based on early or late transition metals from Groups 3 to 10 of the Periodic Table have recently been investigated such as for example those disclosed in Gibson and al. review (Gibson, V. C.; Spitzmesser, S. K., Chem. Rev. 2003, 103, p. 283). But there is still a need to improve either the specificities or the performances of these systems.

It is an aim of the present invention to provide new catalyst components based on macrocyclic ligands.

It is another aim of the present invention to provide active catalyst systems based on these catalyst components.

It is a further aim of the present invention to provide a process for polymerising or for oligomerising ethylene and alpha-olefins with these new catalyst systems.

Accordingly, the present invention discloses ligands of general formula (I) a-f

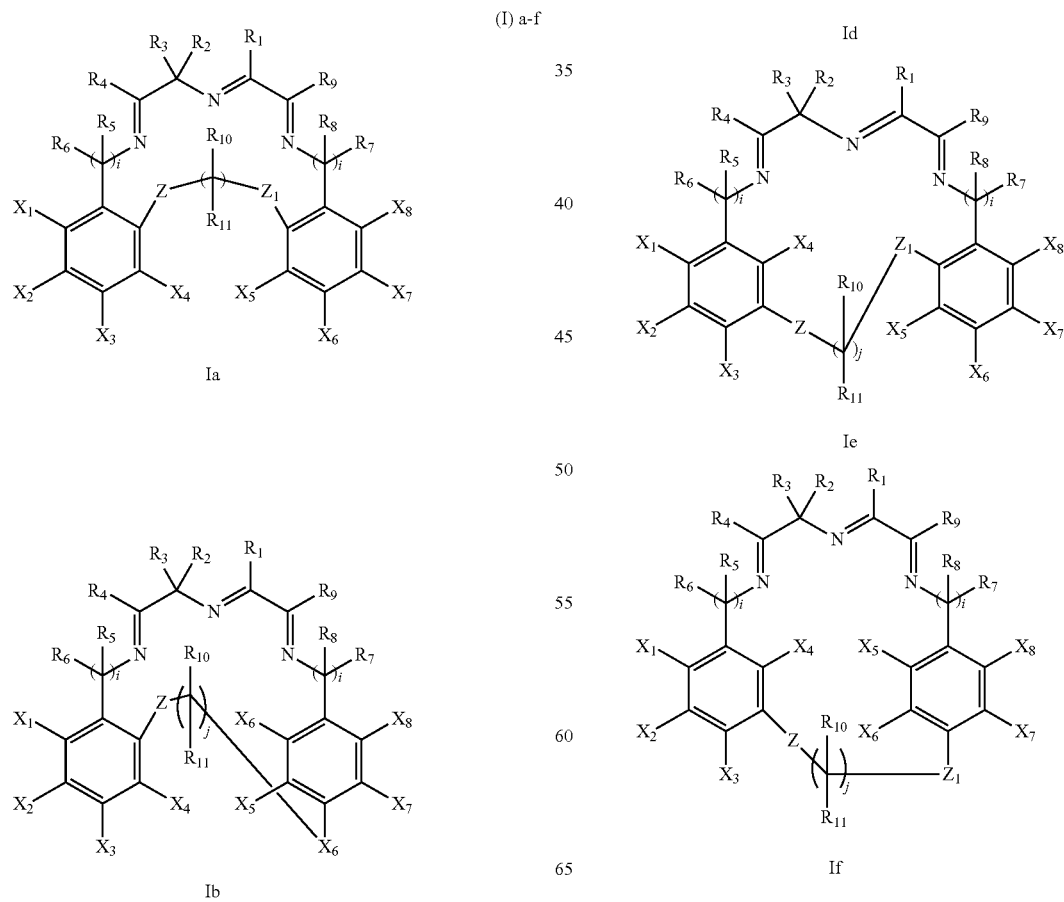

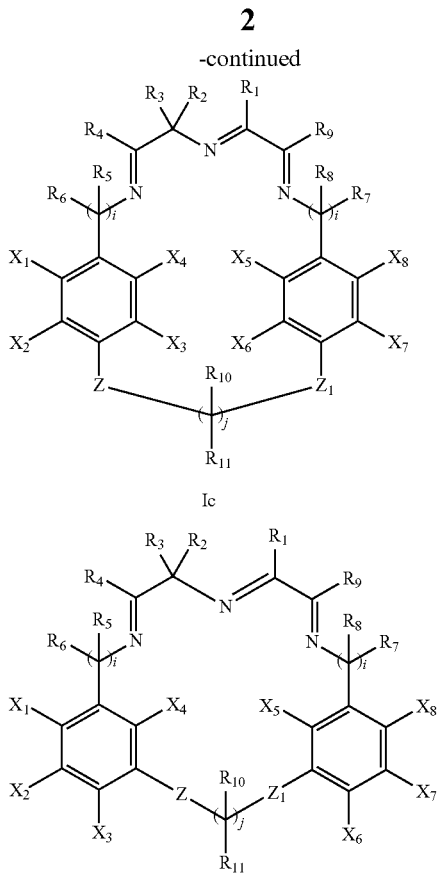

Resulting from the condensation reaction between diamine or dianiline (II) a-f

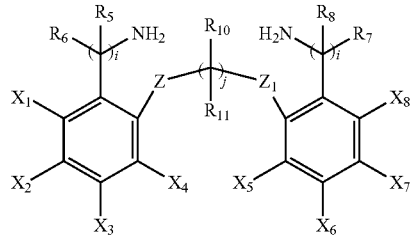
IIa

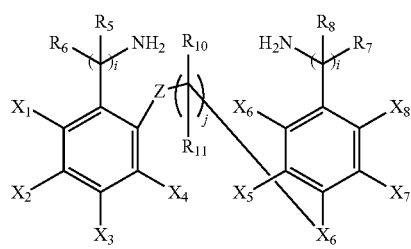
IIb (IIc, IId, IIe structures)

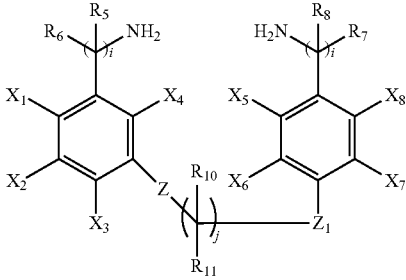
IIf and a ketone or aldehyde of formula (III)

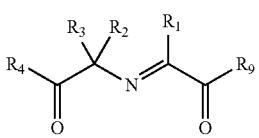
(III)

$R_1$, $R_2$, $R_3$, $R_4$, $R_5$, $R_6$, $R_7$, $R_8$, $R_9$, $R_{10}$ and $R_{11}$ are each independently selected from hydrogen, unsubstituted or substituted hydrocarbyl, or inert functional group, with the restriction that $R_4$ and $R_9$ are not simultaneously OH. Two or more of those groups can themselves be linked together to form further ring or rings.

Z and $Z_1$ can be in position 2, 3 or 4 on the aromatic ring, are the same or different and are selected from groups 14, 15 or 16 of the Periodic Table, $X_1$, $X_2$, $X_3$, $X_4$, $X_5$, $X_6$, $X_7$ and $X_8$ are same or different and are each independently selected from hydrogen, unsubstituted or substituted hydrocarbyl, aromatic, inert functional group or functional group. Most preferably they all are hydrogen.

By inert functional group, is meant preferably a group, other than hydrocarbyl or substituted hydrocarbyl, that is inert under the complexation conditions to which the compound containing said group is subjected. They can be selected for example from halo, ester, ether, amino, imino, nitro, cyano, carboxyl, phosphate, phosphonite, phosphine, phosphinite, thioether and amide. Preferably, they are selected from halo, such as chloro, bromo, fluoro and iodo, or ether of formula —OR* wherein R* is unsubstituted or substituted hydrocarbyl. After metallation of the ligand, an inert functional group must not coordinate to the metal more strongly than the groups organised to coordinate to the metal and thereby displace the desired coordinating group.

i is an integer of from 0 to 10, more preferably 0 or 1 and j is an integer of from 1 to 15, more preferably from 5 to 12.

Preferably, $R_1$, $R_2$, and $R_3$ are joined together to make a cycle, more preferably pyridine.

Preferably, Z and $Z_1$ are selected from O, N, S, P, C and Si, more preferably they are the same and they are O.

The invention also discloses a catalyst component of formula (IV) a-f
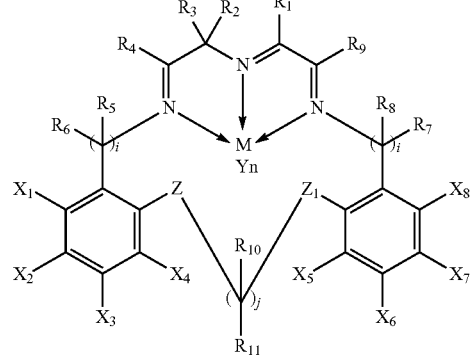
IVa
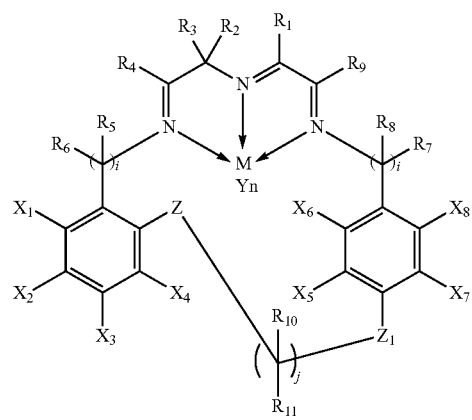
IVb
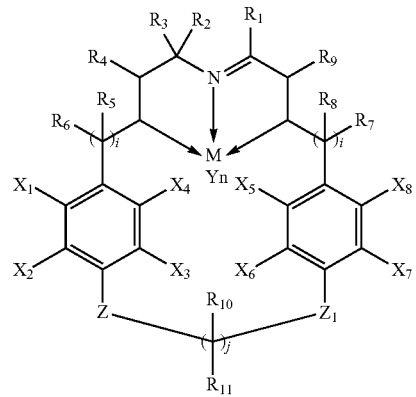
IVc
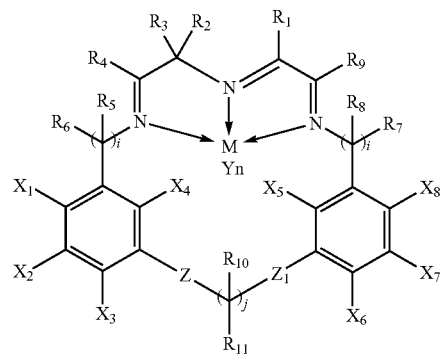
IVd
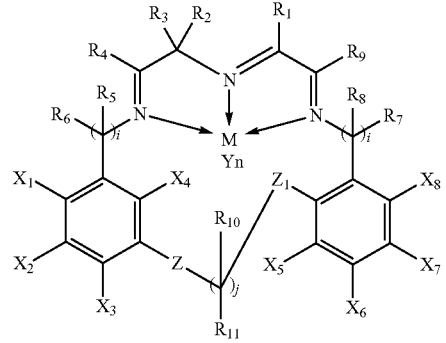
IVe
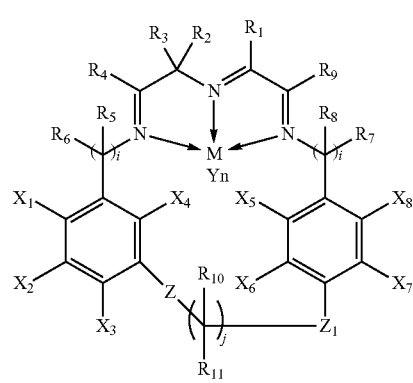
IVf
that is the complexation reaction product of the ligand of formula (I) a-f
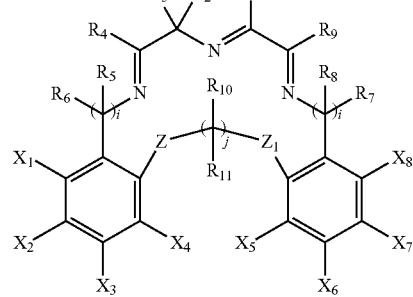
Ia
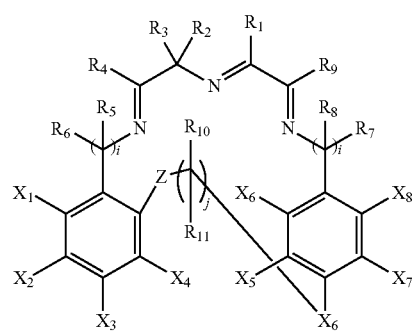
Ib

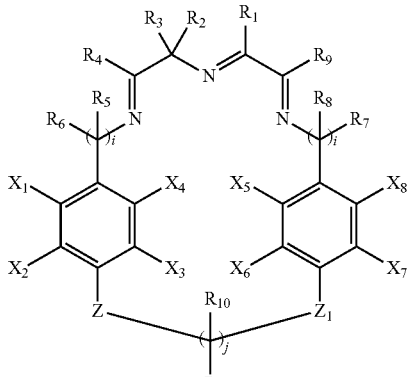

Ic

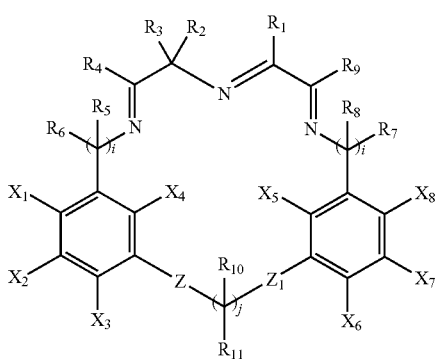

Id

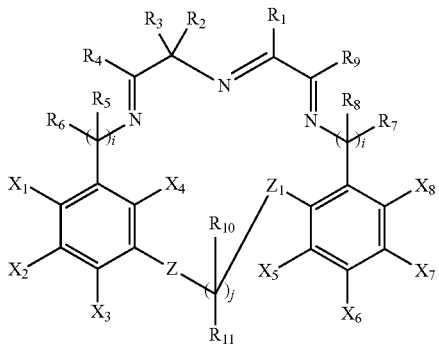

Ie

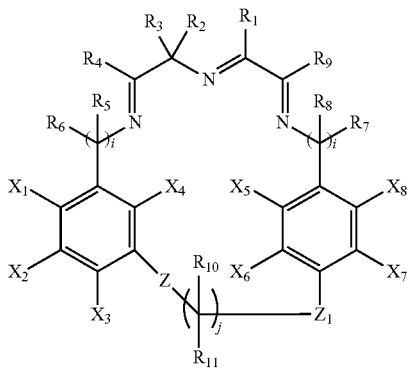

If and a metallic salt of formula $MY_n$ in a solvent, wherein M is a metal Group 3 to 10 of the periodic Table, Y is the same or different and can be a halogen, alcoholate, carboxylate or substituted or unsubstituted hydrocarbyl and n is the valence of M and is 1, 2, 3 or 4.

Preferably, M is Ti, Zr, Hf, V, Cr, Mn, Fe, Co, Ni, Pd or rare earths. More preferably, it is Fe, Cr or V, most preferably it id Fe. Preferably, Y is halogen.

The solvent may be selected from dichloromethane or tetrahydrofuran and the condensation reaction is carried out at room temperature or at reflux.

The present invention also discloses an active catalyst system comprising the single site catalyst component of formula (IV) a-f and an activating agent having an ionising action.

Suitable activating agents are well known in the art. The activating agent can be an aluminium alkyl represented by formula $AlR^+_n X_{3-n}$ wherein $R^+$ is an alkyl having from 1 to 20 carbon atoms and X is a halogen. The preferred alkylating agents are triisobutyl aluminium (TIBAL) or triethyl aluminium (TEAL).

Alternatively, it can be aluminoxane and comprise oligomeric linear and/or cyclic alkyl aluminoxanes represented by formula

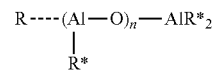

for oligomeric, linear aluminoxanes and by formula

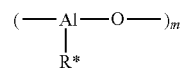

for oligomeric, cyclic aluminoxane,
wherein n is 1-40, preferably 10-20, m is 3-40, preferably 3-20 and $R^*$ is a $C_1$-$C_8$ alkyl group and preferably methyl.

The amount of aluminium-containing activating agent is selected to give an Al/M ratio of from 100 to 3000, preferably of about 2000.

Suitable boron-containing activating agents may comprise a triphenylcarbenium boronate such as tetrakis-pentafluorophenyl-borato-triphenylcarbenium as described in EP-A-0427696, or those of the general formula $[L'-H]+[B\ Ar_1\ Ar_2\ X_3\ X_4]$— as described in EP-A-0277004 (page 6, line 30 to page 7, line 7).

The amount of boron-containing activating agent is selected to give a B/M ratio of from 0.5 to 5, preferably of about 1.

In another embodiment, according to the present invention, the single site catalyst component of formula IV a-f may be deposited on a conventional support. Preferably, the conventional support is a silica impregnated with MAO. Alternatively it can be an activating support such as fluorinated alumina silica.

The present invention further discloses a method for preparing an active catalyst system that comprises the steps of:
a) providing an diamine or dianiline precursor ligand (II) a-f;
b) carrying out a macrocyclisation reaction of the diamine or dianiline ligand precursor of step a) with a ketone or aldehyde (III);
c) retrieving a ligand of formula (I) a-f;
d) complexing the ligand (I) a-f of step c) with a metallic salt $MY_n$;
e) retrieving a catalyst component of formula (IV) a-f;
f) activating with an activating agent having an ionising action;
g) retrieving an active oligomerisation or polymerisation catalyst system.

The active catalyst system is used in the oligomerisation and in the polymerisation of ethylene and alpha-olefins.

The present invention discloses a method for the oligomerisation or the homo- or co-polymerisation of ethylene and alpha-olefins that comprises the steps of:
- a) injecting the active catalyst system into the reactor;
- b) injecting the monomer and optional comonomer;
- c) maintaining under polymerisation conditions;
- d) retrieving the oligomer and/or polymer.

The pressure in the reactor can vary from 0.5 to 50 bars, preferably from 5 to 25 bars.

The polymerisation temperature can range from 10 to 100° C., preferably from 50 to 85° C.

The monomer and optional comonomer are preferably selected from ethylene, propylene or 1-hexene. The optional comonomer may also be a polar functionalised alpha-olefin.

Preferably, the present catalyst system is used for oligomerising ethylene.

Examples

Synthesis of Fe(II) Complexes

Synthesis of bis-cyanoether

Hydroxybenzonitrile, 10 eq of potassium carbonate, 0.5 eq of dibromoalcane and 0.1 eq of sodium iodide were refluxed in butanone under an Argon atmosphere for 22 h. After cooling to room temperature, the mixture was filtered and the solvent was removed under vacuum. The crude residue was washed with pentane and dried in vacuum to yield the desired compound as a colourless solid.

1,9-nonoxybis(4-benzonitrile)

The compound was obtained with a yield of 99% and characterised by NMR.

$^1$H-RMN (300 MHz, CDCl$_3$): δ=1.3-1.6 (br m, 10H), 1.81 (m, 4H), 4.0 (m, 4H), 6.93 (d, 4H), 7.57 (d, 4H).

$^{13}$C-RMN (75 MHz, CDCl$_3$): δ=25.9, 28.0, 28.9, 29.2, 29.4, 33.9, 68.3, 110.0, 115.1, 120.0, 133.9, 162.4.

The same procedure was used to produce a several compounds corresponding to general formula with n varying from 3 to 8.

The yields for different values of n are reported in Table I.

TABLE I

| n | Yield (%) |
|---|---|
| 3 | 99 |
| 4 | 99 |
| 5 | 63 |
| 6 | 63 |
| 8 | 64 |

Other compounds wherein the benzene groups were substituted in various positions were produced following the same procedure. They correspond to general formula The yields for different values of n and for different substituents on the benzene groups are reported in Table II.

TABLE II

| n | R1, R2, R3, R4 | Yield (%) |
|---|---|---|
| 8 | R1 = F, R2 = R3 = R4 = H | 96 |
| 8 | R2 = OMe, R1 = R3 = R4 = H | 99 |
| 8 | R2 = R3 = Br, R1 = R4 = H | 65 |
| 8 | R1 = Cl, R2 = R3 = R4 = H | 84 |
| 4 | R2 = NO$_2$, R1 = R3 = R4 = H | 23 |
| 6 | R2 = NO$_2$, R1 = R3 = R4 = H | 99 |

Synthesis of bis-aminoether

To a solution of THF containing 6 eq of LiAlH$_4$ under argon, the bis cyanoether in anhydrous THF was added dropwise. The solution was refluxed for 3 h. Once cooled to room temperature the solution was cautiously quenched by dropwise addition of water, 15% aq. NaOH solution and water. The aluminium salts were filtered off and the solvent removed under reduced pressure to give the bis-aminoether compound as a colourless solid.

1,9-nonoxybis(4-benzylamine) was synthesised with a yield of 93%. It was characterised by NMR analysis.

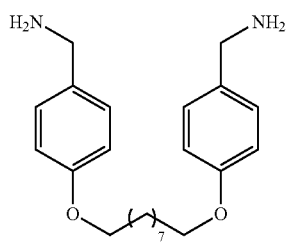

$^1$H-RMN (300 MHz, CDCl$_3$): δ=1.3-1.6 (br m, 10H), 1.78 (m, 4H), 3.80 (s, 4H), 3.94 (m, 4H), 6.86 (d, 4H), 7.21 (d, 4H)

$^{13}$C-RMN (125 MHz, CDCl$_3$): δ=26.4, 29.6, 29.7, 29.9, 46.4, 68.4, 114.9, 128.6, 135.8, 158.4.

The same procedure was used to produce a several compounds corresponding to general formula

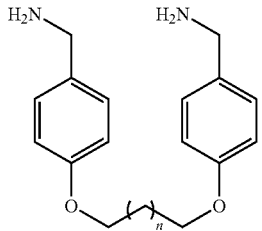

wherein n was varied from 3 to 8. The yields for the different values of n are reported in Table IV.

TABLE IV

| n | Yield (%) |
|---|---|
| 3 | 62 |
| 4 | 83 |
| 5 | 70 |
| 6 | 94 |
| 8 | 91 |

Other compounds wherein the benzene groups were additionally substituted in various positions were also produced following the same procedure. They correspond to formula

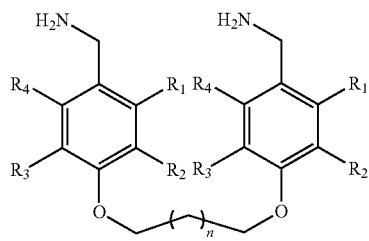

The yields for different values of n and for different substituents on the benzene groups are reported in Table V.

TABLE V

| n | R1, R2, R3, R4 | Yield (%) |
|---|---|---|
| 8 | R1 = F, R2 = R3 = R4 = H | 86 |
| 8 | R2 = OMe, R1 = R3 = R4 = H | 92 |
| 8 | R1 = Cl, R2 = R3 = R4 = H | 67 |
| 4 | R2 = NO$_2$, R1 = R3 = R4 = H | 10 |

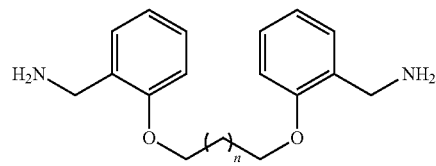

Synthesis of cyclic bis-imino-pyridine

One equivalent of bis-aminoether and 1 equ of 2,6-diacetylpyridine were dissolved in anhydrous ethanol. After addition of a few drops of acetic acid, the reaction mixture was stirred at a temperature of 85° C. for 3 h. The white precipitate was filtered and washed with cold MeOH. The white solid was dried under reduced pressure to yield cyclic bis-imino-pyridine compound with a yield of 63%. The compound was characterised by NMR analysis.

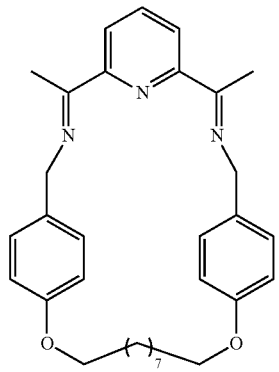

$^1$H-RMN (300 MHz, CDCl$_3$): δ=1.3-1.6 (br m, 10H), 1.77 (m, 4H), 2.52 (s, 6H), 3.96 (m, 4H), 4.72 (s, 4H), 6.90 (d, 4H), 7.35 (d, 4H), 7.71 (t, 1H), 8.20 (d, 2H)

$^{13}$C-RMN (125 MHz, CD$_2$Cl$_2$): δ=14.1, 26.4, 29.7, 29.9, 55.8, 68.4, 114.7, 121.4, 129.2, 133.0, 156.4, 158.4, 167.2.

The same procedure was used to produce a several compounds corresponding to general formula

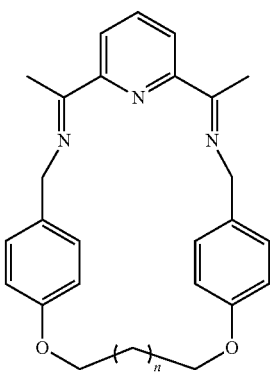

with n varying from 3 to 8. The results are displayed in Table VI.

TABLE VI

| n | Yield (%) |
|---|---|
| 3 | 6 |
| 4 | 35 |
| 5 | 25 |
| 6 | 91 |
| 8 | 49 |

Other compounds wherein the benzene groups were additionally substituted in various positions were also produced following the same procedure. They correspond to formula

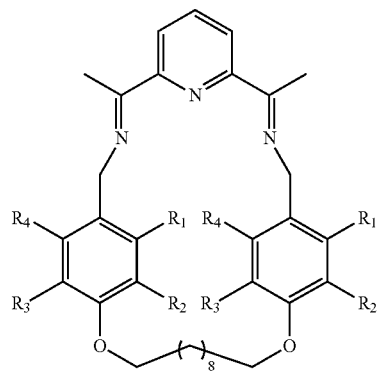

The yields for different substituents on the benzene groups are reported in Table VII.

TABLE VII

| n | R1, R2, R3, R4 | Yield (%) |
|---|---|---|
| 8 | R1 = F, R2 = R3 = R4 = H | 25 |
| 8 | R2 = OMe, R1 = R3 = R4 = H | 23 |

Synthesis of Fe(II) Complexes $FeCl_2 \cdot 4H_2O$ was dried at a temperature of 100° C. under vacuum for 3 h. The cyclic bis-imino-pyridine ligand was dissolved in THF and added to treated $FeCl_2$. After stirring overnight at a temperature of 80° C., the mixture was filtered through a celite pad. The solution was concentrated and pentane was added to give a precipitate. Solvents were filtered off and the solid was washed with pentane. The complex was dried under vacuum, to afford a dark blue powder. The results are summarised in Table VIII.

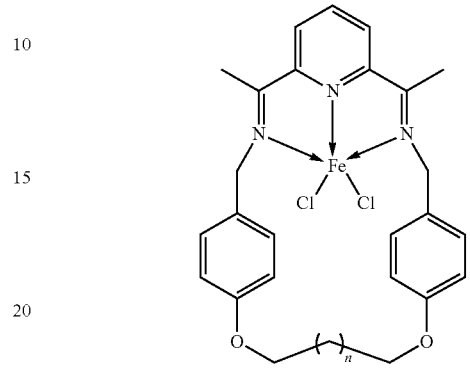

TABLE VIII

| n | Yield (%) |
|---|---|
| 4 | 65 |
| 7 | 64 |
| 8 | 78 |

High Pressure Ethylene Oligomerisation.

Ethylene oligomerisation reactions were performed in a 20 mL stainless steel autoclave containing a glass insert, fitted with mechanical stirring, external thermocouple and pressure gauge and controlled by computer. In a typical reaction run, about 0.5 μmol of the appropriate catalyst were introduced inside the glass insert. The reactor was closed and flushed with argon for 1 hour. 5 mL of a solution of dry toluene and activator were introduced into the reactor. The solution was stirred for 1 hour at a temperature of 50° C. The ethylene pressure was raised to the desired value and continuously fed. After a period of time of 1 hour or an ethylene consumption of 12 mmol, the reaction was quenched with isopropanol and an aliquot analysed by gas chromatography. The gas chromatographic analyses of the reaction products were performed on a Trace GC apparatus with a Petrocol capillary column (methyl silicone, 100 m long, i.d. 0.25 mm and film thickness of 0.5 μm) working at a temperature of 35° C. for a period of time of 15 min and then heated to a temperature of 250° C. at a heating rate of 5° C./min. The remaining reaction mixture was quenched with MeOH/HCl.

The oligomerisation conditions are displayed in Table IX and the results are displayed in Table X. All oligomerisation reactions were performed with about 0.5 μml of iron complex for which n=7 dissolved in 5 mL of the same solvent, at a temperature of 50° C. and under an ethylene pressure of 15 bars.

TABLE IX

| Example | Cocatalyst | [Fe]:[Al]:[Zn] | Amount cata nmol | Time min |
|---|---|---|---|---|
| 1 | Et$_2$AlCl | 1:500:0 | 561 | 60 |
| 2 | ZnEt$_2$ | 1:0:500 | 512 | 60 |
| 3 | MAO | 1:500:0 | 528 | 60 |

TABLE IX-continued

| Example | Cocatalyst | [Fe]:[Al]:[Zn] | Amount cata nmol | Time min |
|---|---|---|---|---|
| 4 | MAO | 1:2000:0 | 496 | 60 |
| 5 | MAO/ZnEt$_2$ | 1:100:500 | 480 | 60 |
| 6 | MAO/ZnEt$_2$ | 1:500:500 | 528 | 60 |

TABLE X

| | C2 cons. | | %C4 | | %C6 | | |
|---|---|---|---|---|---|---|---|
| Ex. | mmol | Activity * | Total | %α-C4 | Total | %α-C6 | %>C6 |
| 1 | 0.76 | 38 | no oligomer detected | | | | |
| 2 | 0.56 | 31 | no oligomer detected | | | | |
| 3 | 1.58 | 84 | 61 | 99 | 23 | 88 | 16 |
| 4 | 4.52 | 255 | 57 | 99 | 26 | 83 | 17 |
| 5 | 1.17 | 69 | 59 | 99 | 19 | 83 | 22 |
| 6 | 0.58 | 31 | traces of C4 to C12 | | | | |

* activities are expressed in kg of consumed ethylene per mole of Fe per hour.

The invention claimed is:

1. An active catalyst system comprising:
a) a metallic component selected from formulas IVa to IVf

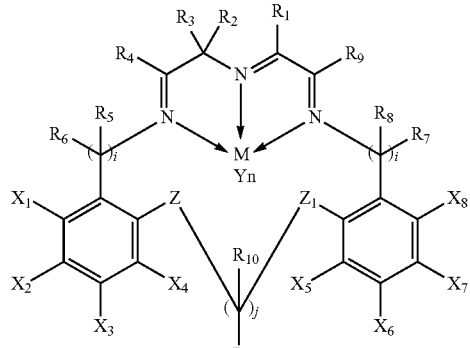

IVa

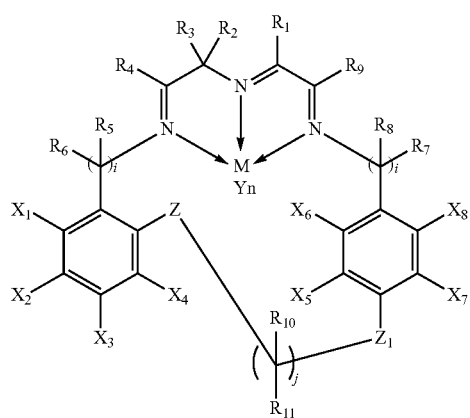

IVb

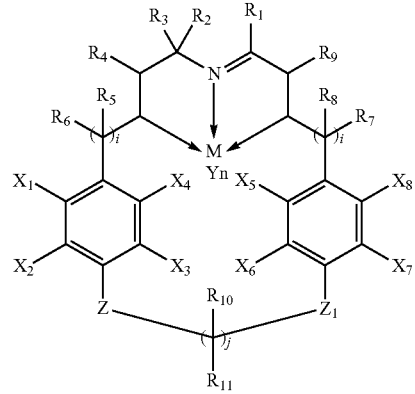

IVc

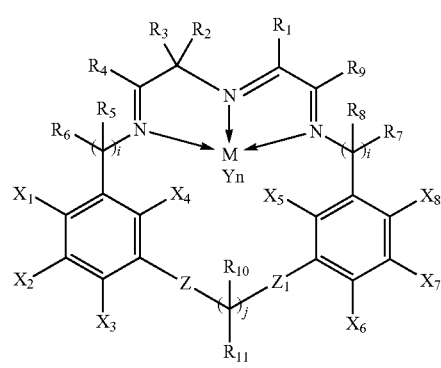

IVd

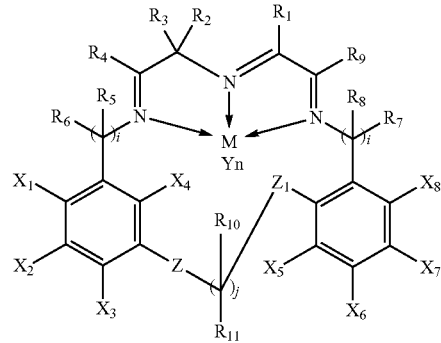

IVe

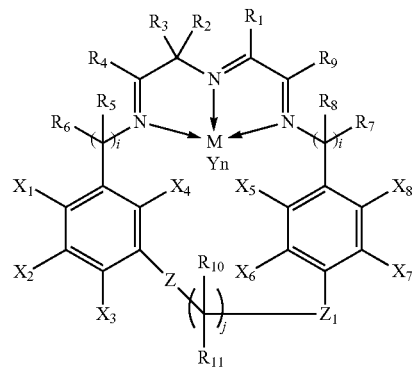

IVf resulting from complexing the ligand selected from formulas Ia to If

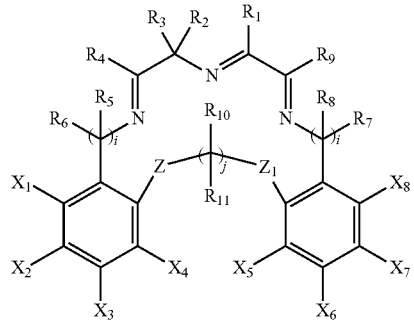

Ia

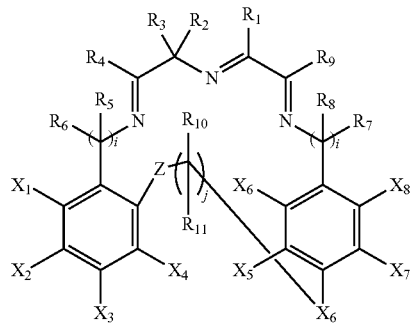

Ib

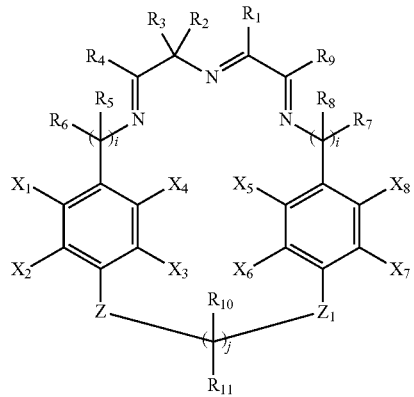

Ic

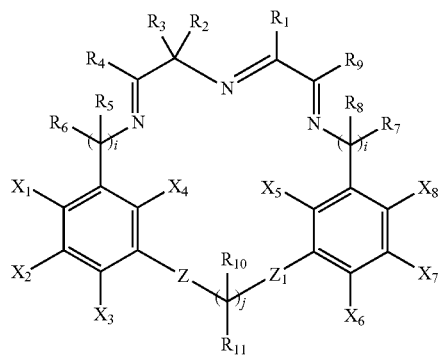

Id

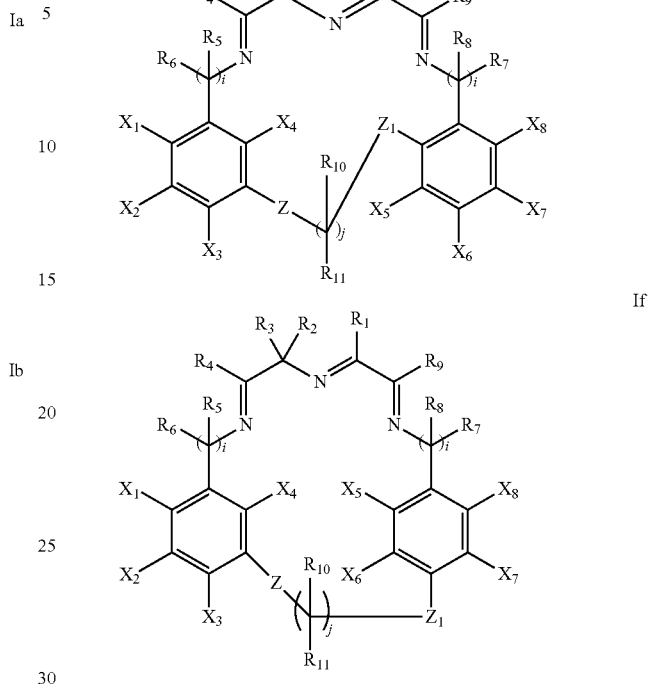

Ie

If with a metallic salt $MY_n$; wherein M is a metal group 3 to 10 of the Periodic Table, Y is the same or different and is a halogen, alcoholate, carboxylate or substituted or unsubstituted hydrocarbyl and n is the valence of M; wherein $R_1$, $R_2$, $R_3$, $R_4$, $R_5$, $R_6$, $R_7$, $R_8$, $R_9$, $R_{10}$ and $R_{11}$ are the same or different and are each independently selected from hydrogen, unsubstituted or substituted hydrocarbyl, or inert functional group, with the restriction that $R_4$ and $R_9$ are not simultaneously OH, and wherein two or more substituents can be linked together to form further ring or rings, wherein Z and $Z_1$ can be in position 2, 3 or 4 on the aromatic ring, are the same and are O, wherein $X_1$, $X_2$, $X_3$, $X_4$, $X_5$, $X_6$, $X_7$ and $X_8$ are the same or different and are each independently selected from hydrogen, unsubstituted or substituted hydrocarbyl, aromatic, or inert functional group, and wherein i is an integer of from 0 to 10 and j is an integer of from 1 to 15; and b) an activating agent having an ionizing action.

2. The active catalyst system of claim 1 wherein $R_1$, $R_2$ and $R_3$ are joined together to make a ring.

3. The active catalyst system of claim 1 wherein $X_1$, $X_2$, $X_3$, $X_4$, $X_5$, $X_6$, $X_7$ and $X_8$ are the same and are hydrogen.

4. The active catalyst system of claim 1 wherein i is 0 or 1 and j is an integer from 5 to 12.

5. The active catalyst system of claim 1 wherein M is Fe, Cr or V.

6. The active catalyst system of claim 1 wherein the activating agent is fluorinated activating support.

* * * * *